(12) United States Patent
Sabbagh

(10) Patent No.: US 8,303,305 B2
(45) Date of Patent: Nov. 6, 2012

(54) TONGUE RETRACTOR AND FLUID/PARTICLE BARRIER

(76) Inventor: Emily M. Sabbagh, Gig Harbor, WA (US)

(*) Notice: Subject to any disclaimer, the term of this patent is extended or adjusted under 35 U.S.C. 154(b) by 0 days.

(21) Appl. No.: 13/080,878

(22) Filed: Apr. 6, 2011

(65) Prior Publication Data

US 2011/0183288 A1 Jul. 28, 2011

Related U.S. Application Data

(63) Continuation of application No. 11/195,382, filed on Aug. 2, 2005, now Pat. No. 7,938,644.

(51) Int. Cl.
*A61C 5/14* (2006.01)
*A61C 5/00* (2006.01)
(52) U.S. Cl. ........................... 433/136; 433/140
(58) Field of Classification Search ............... 433/136, 433/137, 140, 93; 604/358, 374, 385.01
See application file for complete search history.

(56) References Cited

U.S. PATENT DOCUMENTS

| 4,293,301 | A | * | 10/1981 | Mattsson | 433/136 |
| 4,813,872 | A | * | 3/1989 | Knitter | 433/136 |
| 5,573,400 | A | * | 11/1996 | Asher | 433/136 |
| 5,749,729 | A | * | 5/1998 | Skinner et al. | 433/136 |
| 2003/0031980 | A1 | * | 2/2003 | Owais | 433/136 |
| 2006/0041987 | A1 | * | 3/2006 | Villain | 2/53 |

* cited by examiner

*Primary Examiner* — Heidi M Eide
(74) *Attorney, Agent, or Firm* — Frommer Lawrence & Haug LLP; Patrick R. Turner

(57) ABSTRACT

Various embodiments of the present invention are directed to a tongue retractor and fluid/particle barrier for use in medical procedures performed in and around a patient's mouth. In one embodiment of the present invention, a kidney-shaped tongue retractor and fluid/particle barrier, with an insertion end and a handling end, is inserted into the mouth of a patient. The insertion end of the tongue retractor and fluid/particle barrier is specifically positioned to isolate and protect the patient's tongue from the medical procedure and to protect the patient from inhaling or swallowing fluids and scattered debris.

9 Claims, 5 Drawing Sheets

TONGUE RETRACTOR AND FLUID/PARTICLE BARRIER

CROSS-REFERENCE TO RELATED APPLICATIONS

This patent application is a continuation of U.S. patent application Ser. No. 11/195,382 filed on Aug. 2, 2005, which is incorporated herein by reference.

TECHNICAL FIELD

The present invention relates to the field of oral medical devices, and, in particular, to a tongue retractor and fluid/particle barrier for use during oral medical procedures.

BACKGROUND OF THE INVENTION

Oral healthcare professionals, such as oral surgeons, dentists, periodontists, orthodontists, and endodontists, perform various types of oral surgeries and dental procedures, collectively referred to as "oral procedures," on patients each year. Depending on the nature of the oral procedure being performed, patients may be placed in various levels of consciousness using various types of anesthesia. For some procedures, patients may be fully conscience, while for other procedures, patients may be fully sedated. Patients may be given local anesthesia or general anesthesia. A patient may react in various ways to instruments placed in the patient's mouth, may experience different levels of discomfort, and may have different abilities to guard against swallowing or inhaling fluids and particles created during oral procedures, depending on the type of anesthesia, duration of administration of anesthesia, and the concentration of the anesthesia administered.

Tongue retraction, fluid build-up, and debris scatter are common occurrences during oral procedures. A patient's tongue is often retracted during an oral procedure to give the oral health care professional ample room to work, and to protect the patient's tongue from injury. Oral procedures often promote accumulation of various fluids in a patient's mouth, including saliva, blood, and fluids used to irrigate dental instruments. Suction is often used to assist with fluid removal in a patient's mouth, but additional means for fluid removal are often needed. Oral procedures often create large amounts of particles, or debris, in and around a patient's mouth. Broken teeth, tartar, crowns, bridges, metals, ceramics, and other materials may accumulate in and around a patient's mouth and make the patient vulnerable to swallowing or inhaling the loose debris. Additional debris may also be introduced into a patient's mouth by a health care professional during an oral procedure.

Wads of gauze are often used by oral health care professionals to retract a patient's tongue during an oral procedure, to absorb excess fluids, and to provide a barrier to prevent the patient from swallowing or inhaling debris. However, use of gauze has disadvantages. Gauze is generally not sufficiently rigid and is often dislodged. Gauze is also often insufficiently absorbent. As a result, gauze often needs to be changed numerous times during oral procedures. Gauze is typically an ineffective particle barrier. Wads of gauze can be bulky and provide an irregular surface around which a health care professional may need to maneuver during an oral procedure. During oral procedures involving a drill, an oral health-care professional is likely to nick the gauze with the drill bur. When a spinning drill bur contacts gauze, the gauze often becomes entangled in the drill bur, and the gauze begins to spin with the bur. Any debris and fluid that are held in the gauze tend to scatter. The oral health professional needs to turn off the drill, untangle the gauze from the bur, clean off the patient, and make sure the patient is not choking on fluid and/or debris that may have entered the patient's throat. During normal use, gauze may also contact the back of a patient's tongue, causing a gag reflex.

Rubber dams are also commonly used to shield the patient from swallowing or inhaling particles during oral procedures. Rubber dams are thin sheets of rubber, held in place with a clamp and frame, which stretch around a procedural site. Although rubber dams can be an effective way to protect patients from swallowing and inhaling scattered debris during oral procedures, some patients express a high degree of discomfort and agitation when a rubber dam is inserted into their mouths. Some patients feel like they are suffocating and begin to panic.

Dentists, oral surgeons, and other oral health care professionals have, therefore, recognized a need for a tongue retractor and fluid/particle barrier that can retract a patient's tongue and form an effective fluid/particle barrier to protect the patient from swallowing or inhaling fluid and particles created during an oral procedure.

SUMMARY OF THE INVENTION

Various embodiments of the present invention are directed to a tongue retractor and fluid/particle barrier for use in medical procedures performed in and around a patient's mouth. In one embodiment of the present invention, a kidney-shaped tongue retractor and fluid/particle barrier, with an insertion end and a handling end, is inserted into the mouth of a patient. The insertion end of the tongue retractor and fluid/particle barrier is specifically positioned to isolate and protect the patient's tongue from the medical procedure and to protect the patient from inhaling or swallowing fluids and scattered debris.

DETAILED DESCRIPTION OF THE INVENTION

Various embodiments of the present invention are directed to a tongue retractor and fluid/particle barrier, referred to as an "oral shield," for use in oral procedures. The oral shield is inserted into the mouth of a patient and positioned to provide room for an oral health care professional to perform an oral procedure, while also protecting the patient's tongue from possible damage caused by the oral procedure. The oral shield also absorbs fluids that tend to build up in a patient's mouth during oral procedures, and minimizes swallowing and inhaling of debris by the patient during the oral procedure.

Figure 1:
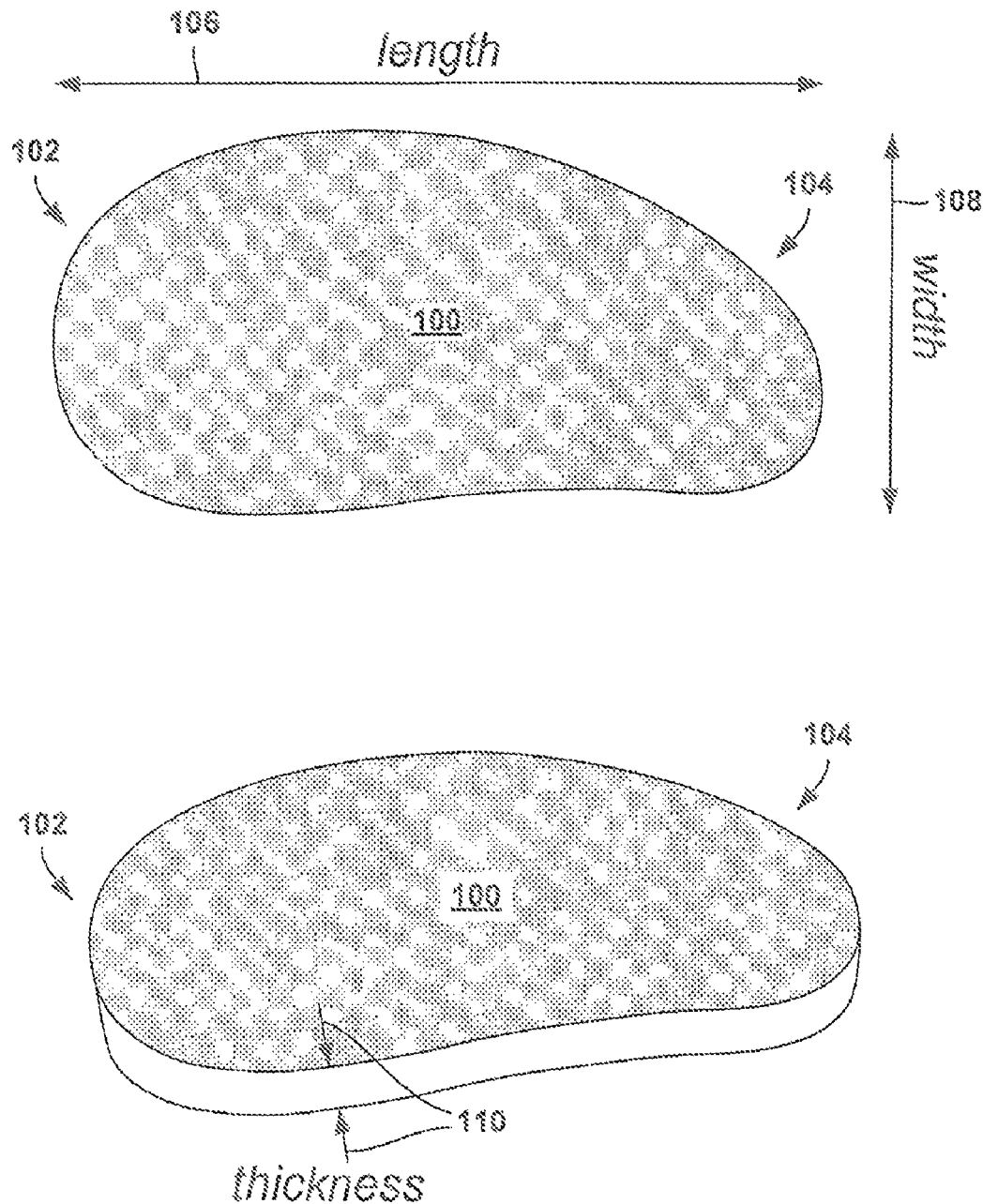
FIG. 1 shows a top view and a perspective view of one of many embodiments of an oral shield.

FIG. 1 shows a top view and a perspective view of one of many embodiments of an oral shield. Oral shield 100 is kidney-shaped, with insertion end 102 and handling end 104. Insertion end 102 is slightly larger than handling end 104.

Oral shield 100 is stippled in FIG. 1, and in later figures, to distinguish oral shield 100 from other hardware. Oral shield 100 is constructed from an absorbent, non-toxic, porous rubber or cellulose material, acceptable materials including sponge, sponge cloth, etc. The shape and dimensions of oral shield 100 are designed to fit the contours of a mouth, as discussed with reference to subsequent figures. For an adult mouth, an oral shield with length 106 of approximately 90 millimeters and width 108 of approximately 50 millimeters provides effective tongue retraction and fluid/particle shielding. An oral shield with thickness 110 of approximately 5 millimeters has also been shown to provide effective absorbency and provide adequate protection and rigidity, while still being sufficiently thin to not be overly obtrusive. For a child's mouth, an oral shield with a length of approximately 70 millimeters and a width of approximately 40 millimeters provides effective tongue retraction and fluid/particle shielding.

Many oral procedures take an extended period of time to perform. Many patients find it difficult to keep their mouths open for long periods without assistance. Moreover, patients may be given various types of anesthesia, increasing the difficulty for a patient to keep his or her mouth open for the duration of an oral procedure. Bite guards are often used to hold a patient's mouth open while an oral health care professional is performing an oral procedure. Bite guards provide a rigid support for a patient's teeth to clench while preventing the patient's mouth from closing. Bite guards work in tandem with tongue retractors to provide an oral health care professional access to an oral-procedural site. In addition to providing access to a patient's mouth, bite guards also keep a patient from biting an oral health care professional while he or she is working within a patient's mouth.

Figure 2:
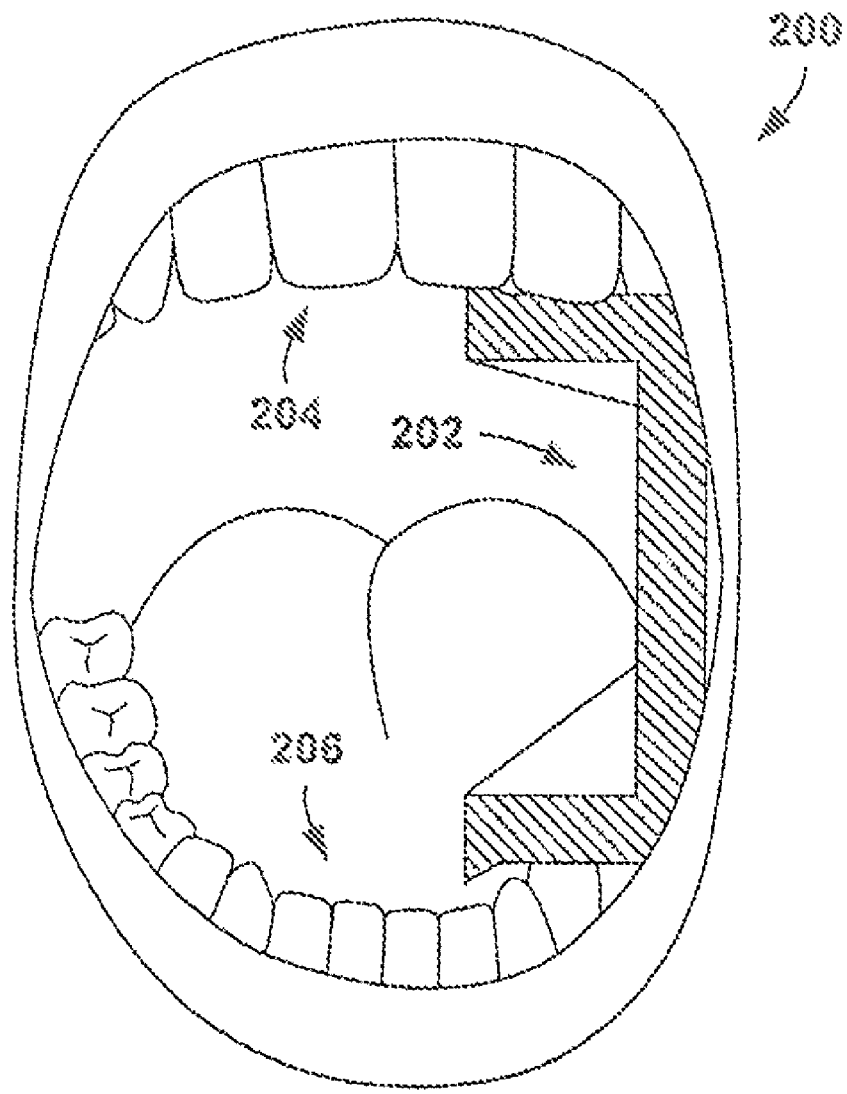
FIG. 2 illustrates a mouth held open by a bite guard inserted between a patient's upper teeth and lower teeth.

FIG. 2 illustrates a mouth held open by a bite guard inserted between a patient's upper teeth and lower teeth. Open mouth 200 contains bite guard 202 inserted between upper teeth 204 and lower teeth 206. The front edge of bite guard 202 is shown cross-hatched in FIG. 2, and in other figures, to distinguish bite guard 202 from other hardware. Bite guard 202 is generally placed on the opposite side of the mouth from an oral-procedural site. For example, when an oral procedure is performed on the right side of the patient's mouth, bite guard 202 is often placed on the left side of the mouth, as shown in FIG. 2.

Figure 3:
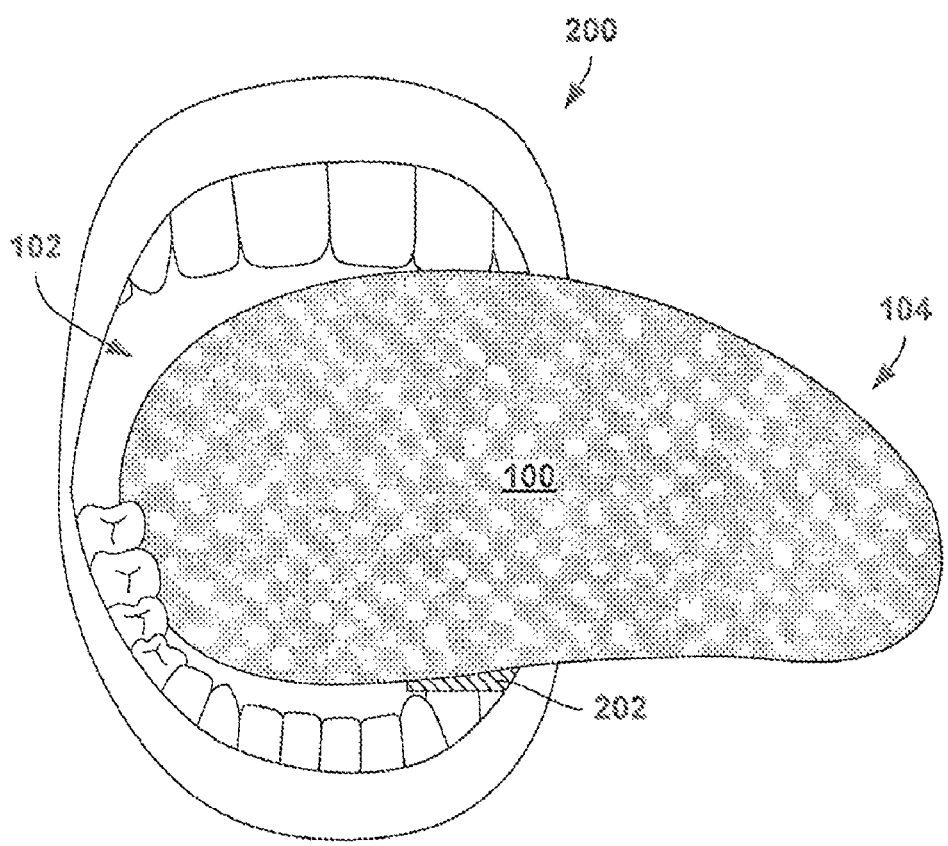
FIG. 3 illustrates one embodiment of an oral shield partially inserted into a patient's mouth.

FIG. 3 illustrates one embodiment of an oral shield partially inserted into a patient's mouth. Insertion end 102 of oral shield 100 is shown partially inserted into open mouth 200. Insertion end 102 is positioned laterally to the patient's tongue on the side of the mouth opposite from bite guard 300. In other words, oral shield 100 is placed on the same side of a mouth as the site of the oral procedure. Handling end 104 of oral shield 100 can be used to insert, position, and remove oral shield 100 from a patient's mouth.

Figure 4:
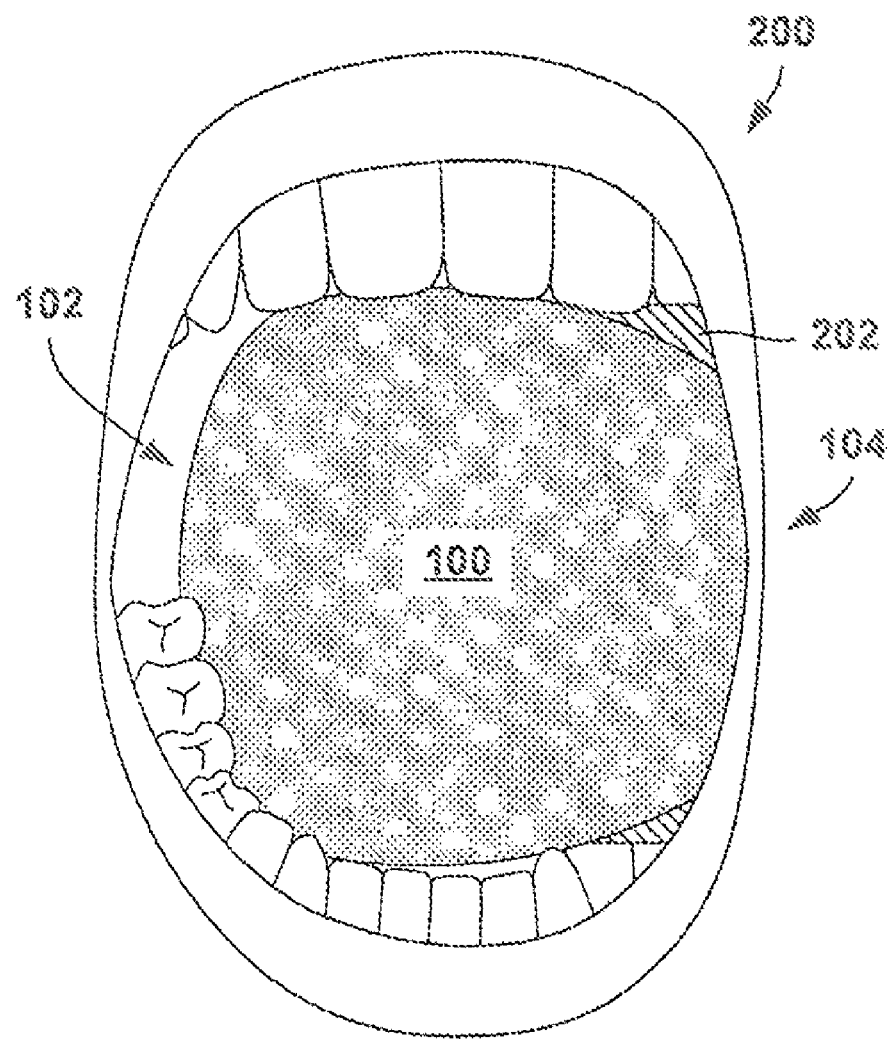
FIG. 4 illustrates one embodiment of an oral shield fully inserted into a patient's mouth.

FIG. 4 illustrates one embodiment of an oral shield fully inserted into a patient's mouth. Insertion end 102 of oral shield 100 is shown positioned on the right side of the patient's mouth, lateral to the patient's tongue and medial to the patient's teeth. Handling end 104 of oral shield 100 is on the left side of the patient's mouth, tucked between the lateral edge of bite block 300 and the buccal mucosa of the patient's left cheek. When a patient cannot use a bite block, such as when a patient has only a limited range of motion of his or her temporomandibular joint, handling end 104 of oral shield 100 can be secured loosely within a patient's mouth, lateral to the patient's teeth and medial to buccal mucosa of the patient's cheek.

The insertion end of an oral shield is approximately shaped to the contours of an average adult oral cavity and provides a thin, flexible barrier between a patient's teeth and tongue that extends from the patient's palate, at the roof of a mouth, to the patient's mylohyoid muscle, at the floor of a mouth. When an oral shield is inserted into a patient's mouth, as shown in FIG. 4, with the insertion end of the oral shield on the right side of the patient's mouth and the handling end on the left side of the patient's mouth, the patient's tongue and posterior pharynx are effectively isolated from the right side of the patient's mouth and an absorbent barrier is in place that shields particles and absorbs fluids created while oral procedures are performed on either the upper or lower right side of the patient's mouth.

Figure 5:
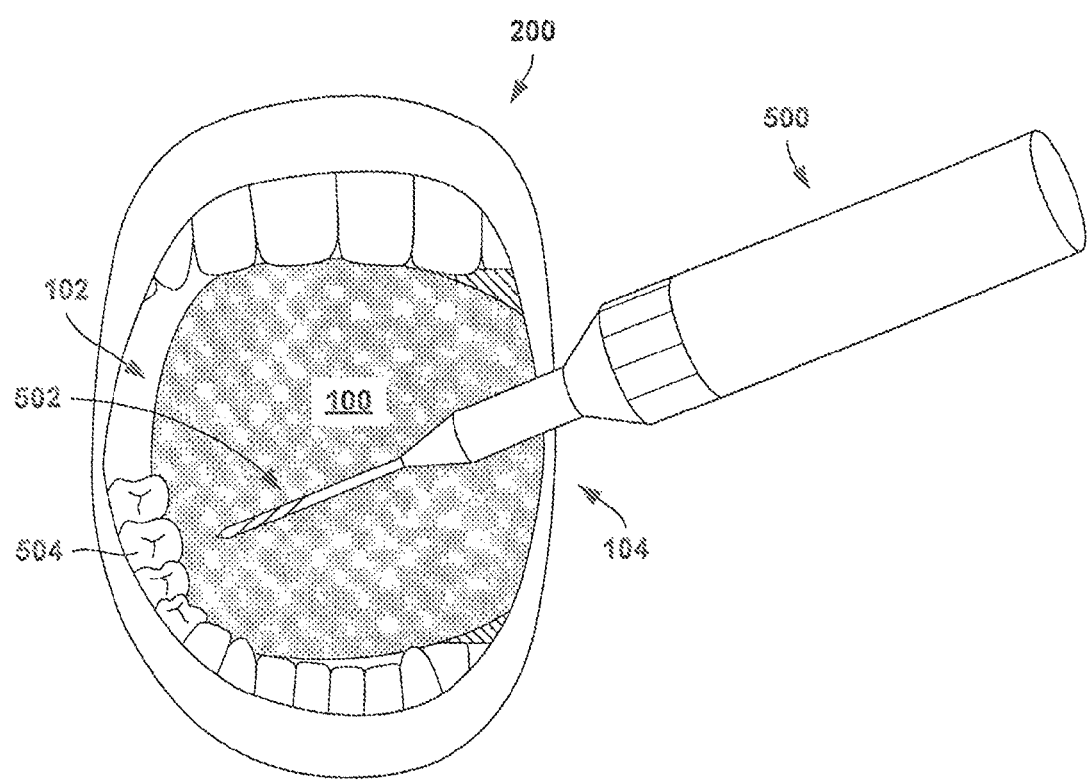
FIG. 5 shows one embodiment of an oral shield in the mouth of a patient who is about to undergo a procedure involving a dental drill.

FIG. 5 shows one embodiment of an oral shield in the mouth of a patient who is about to undergo a procedure involving a dental drill. Oral shield 100 is placed within open mouth 200. Insertion end 102 is positioned on the right side of the patient's mouth, lateral to the patient's tongue and medial to the patient's teeth. Handling end 104 is inserted between the lateral side of bite block 202 and the buccal mucosa of the patient's left cheek. Drill 500 is shown with bur 502 near tooth 504.

An oral health care professional can position an oral shield into the mouth of a patient, as shown in FIG. 5, and perform an oral procedure on the patient. For example, the oral health care professional can use drill 500 to drill a hole in tooth 504. When bur 502 is powered, bur 502 rotates at a high rate of speed. As bur 502 drills a hole in tooth 504, pieces of tooth 504 can scatter in and around the patient's mouth. Bur 502 may also be irrigated during tooth drilling. Water, or other fluids used for bur irrigation, may accumulate in the patient's mouth along with blood and saliva. Oral shield 100 blocks bits of tooth 504 from falling down the patient's throat. Oral shield 100 also absorbs fluids and prevents accumulation of fluids, including irrigation fluids, blood, and saliva, in the patient's throat. When oral shield 100 becomes saturated with fluids, oral shield 100 can be removed and wrung out to dispose of absorbed fluids. Oral shield 100 can then be reinserted into the patient's mouth. When a bur nicks oral shield 100, a small nick may be created in oral shield 100 where bur 502 contacted oral shield 100. However, small nicks usually do not affect the performance of oral shield 100. Likewise, there is typically no interruption of the performance of the bur.

Although the present invention has been described in terms of a particular embodiment, it is not intended that the invention be limited to this embodiment. In another embodiment of the present invention, an oral shield is impregnated with flavorings to ameliorate discomfort which may be associated by some people with undergoing an oral procedure. Flavorings could be in many possible variations that may be pleasing to both adults and children. For adults, appealing flavors may include spearmint, peppermint, and cinnamon. For children, appealing flavors may include fruit punch, grape, bubble gum, and cherry.

In yet another embodiment of the present invention, an oral shield is impregnated with an anesthetic, such as 1% xylocaine. In another embodiment of the present invention, an oral shield is impregnated with an antibacterial agent, such as chlorhexidine gluconate oral rinse. Any combination of two or more impregnations may be used concurrently. For example, an oral shield can be concurrently impregnated with bubble gum flavoring and 1% xylocaine. As another example, an oral shield can be concurrently impregnated with cinnamon and a chlorhexidine gluconate oral rinse.

Additional modifications within the spirit of the invention will be apparent to those skilled in the art. For example, dimensional changes to an oral shield can be made to accommodate patients with unusually-shaped mouths. Thicknesses of an oral shield may be varied, as well, to increase rigidity and/or absorbency. Since oral procedures are commonly performed on children, it may be advantageous to make an oral shield appear more inviting to a child patient. In addition to impregnating an oral shield with an enticing flavor, oral shields could be made in a variety of colors. Interesting designs, patterns, and likenesses of familiar literary and media characters could also be displayed on oral shields.

The foregoing detailed description, for purposes of illustration, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Obviously many modifications and variation are possible in view of the above teachings. The embodiments were chosen and described in order to best explain the principles of the invention and its practical applications and to thereby enable others skilled in the art to best utilize the invention and various embodiments with various modifications as are suited to the particular use contemplated.

What is claimed as new and desired to be protected by Letters Patent of the United States is:

1. An oral shield for use in oral medical procedures, the oral shield comprising:
    an absorbent, deformable shield body having a circumference, the shield body comprising
        an insertion end configured and arranged for insertion into a patient's mouth, the insertion end having an outer edge that comprises a convex region that extends an entire length of the outer edge of the insertion end,
        a handling end disposed opposite to the insertion end, the handling end having an outer edge that comprises a convex region that extends an entire length of the outer edge of the handling end, wherein the insertion end is larger in size than the handling end,
        a first curved outer edge extending between the insertion end and the handling end, and
        a second curved outer edge extending between the insertion end and the handling end, wherein the second curved outer edge is disposed opposite to the first curved outer edge;
    wherein the outer edge of the insertion end, the outer edge of the handling end, the first curved outer edge, and the second curved outer edge collectively form the entire circumference of the shield body;
    wherein the first curved outer edge comprises a single concave region, and wherein the first curved outer edge is shaped to correspond to the contours of a floor of a patient's mouth along an anterior-posterior axis between inner surfaces of the patient's teeth and the patient's tongue;
    wherein the second curved outer edge comprises a convex region extending an entire length of the second curved outer edge, and wherein the second curved outer edge is shaped to the contours of a roof of the patient's mouth along an anterior-posterior axis between inner surfaces of the patient's teeth and the patient's tongue;
    wherein the shield body is configured and arranged such that when the insertion end is inserted into a first side of the patient's mouth, between inner surfaces of the patient's teeth and the patient's tongue, the first curved outer edge abuts the floor of the patient's mouth while the second curved outer edge simultaneously abuts the roof of the patient's mouth, and while at least a portion of the handling end extends outward from the mouth;
    wherein the handling end is configured and arranged such that, when the insertion end is inserted into the first side of the patient's mouth, the portion of the handling end extending outward from the mouth is tuckable between outer surfaces of the patient's teeth and an inner surface of the patient's cheek on a second side of the patient's mouth, opposite to the first side of the patient's mouth, to isolate the patient's tongue and posterior pharynx from the first side of the patient's mouth,
    wherein the oral shield is constructed entirely from an absorbent, non-toxic, porous rubber or cellulose material.

2. The oral shield of claim 1, wherein the shield body has a length that is greater than a length of the patient's mouth along an anterior-posterior axis.

3. The oral shield of claim 1, wherein the shield body has a length of at least 60 millimeters.

4. The oral shield of claim 1, wherein the shield body has a width of at least 35 millimeters.

5. The oral shield of claim 1, wherein the shield body has a thickness of at least 3 millimeters.

6. An oral shield for use in oral medical procedures, the oral shield comprising:
    an absorbent, deformable shield body having a circumference, the shield body comprising
        an insertion end configured and arranged for insertion into a patient's mouth, the insertion end having an outer edge that comprises a convex region that extends an entire length of the outer edge of the insertion end,
        a handling end disposed opposite to the insertion end, the handling end having an outer edge that comprises a convex region that extends an entire length of the outer edge of the handling end, wherein the insertion end is larger in size than the handling end,
        a first curved outer edge extending between the insertion end and the handling end, and
        a second curved outer edge extending between the insertion end and the handling end, wherein the second curved outer edge is disposed opposite to the first curved outer edge;
    wherein the outer edge of the insertion end, the outer edge of the handling end, the first curved outer edge, and the second curved outer edge collectively form the entire circumference of the shield body;
    wherein the first curved outer edge comprises a single concave region, and wherein the first curved outer edge is shaped to correspond to the contours of a floor of a patient's mouth along an anterior-posterior axis between inner surfaces of the patient's teeth and the patient's tongue:
    wherein the second curved outer edge comprises a convex region extending an entire length of the second curved outer edge, and wherein the second curved outer edge is shaped to the contours of a roof of the patient's mouth along an anterior-posterior axis between inner surfaces of the patient's teeth and the patient's tongue;
    wherein the shield body is configured and arranged such that when the insertion end is inserted into a first side of the patient's mouth, between inner surfaces of the patient's teeth and the patient's tongue, the first curved outer edge abuts the floor of the patient's mouth while the second curved outer edge simultaneously abuts the roof of the patient's mouth, and while at least a portion of the handling end extends outward from the mouth;

wherein the handling end is configured and arranged such that, when the insertion end is inserted into the first side of the patient's mouth, the portion of the handling end extending outward from the mouth is tuckable between outer surfaces of the patient's teeth and an inner surface of the patient's cheek on a second side of the patient's mouth, opposite to the first side of the patient's mouth, to isolate the patient's tongue and posterior pharynx from the first side of the patient's mouth;

wherein the oral shield is constructed entirely from at least one of sponge or sponge cloth.

7. An oral shield for use in oral medical procedures, the oral shield comprising:

an absorbent, deformable shield body having a circumference, the shield body comprising an insertion end configured and arranged for insertion into a patient's mouth, the insertion end having an outer edge that comprises a convex region that extends an entire length of the outer edge of the insertion end, a handling end disposed opposite to the insertion end, the handling end having an outer edge that comprises a convex region that extends an entire length of the outer edge of the handling end, wherein the insertion end is larger in size than the handling end, a first curved outer edge extending between the insertion end and the handling end, and a second curved outer edge extending between the insertion end and the handling end, wherein the second curved outer edge is disposed opposite to the first curved outer edge;

wherein the outer edge of the insertion end, the outer edge of the handling end, the first curved outer edge, and the second curved outer edge collectively form the entire circumference of the shield body;

wherein the first curved outer edge comprises a single concave region, and wherein the first curved outer edge is shaped to correspond to the contours of a floor of a patient's mouth along an anterior-posterior axis between inner surfaces of the patient's teeth and the patient's tongue;

wherein the second curved outer edge comprises a convex region extending an entire length of the second curved outer edge, and wherein the second curved outer edge is shaped to the contours of a roof of the patient's mouth along an anterior-posterior axis between inner surfaces of the patient's teeth and the patient's tongue;

wherein the shield body is configured and arranged such that when the insertion end is inserted into a first side of the patient's mouth, between inner surfaces of the patient's teeth and the patient's tongue, the first curved outer edge abuts the floor of the patient's mouth while the second curved outer edge simultaneously abuts the roof of the patient's mouth, and while at least a portion of the handling end extends outward from the mouth;

wherein the handling end is configured and arranged such that, when the insertion end is inserted into the first side of the patient's mouth, the portion of the handling end extending outward from the mouth is tuckable between outer surfaces of the patient's teeth and an inner surface of the patient's cheek on a second side of the patient's mouth, opposite to the first side of the patient's mouth, to isolate the patient's tongue and posterior pharynx from the first side of the patient's mouth;

wherein the oral shield comprises a flavoring impregnated into the oral shield.

8. An oral shield for use in oral medical procedures, the oral shield comprising:

an absorbent, deformable shield body having a circumference the shield body comprising an insertion end configured and arranged for insertion into a patient's mouth, the insertion end having an outer edge that comprises a convex region that extends an entire length of the outer edge of the insertion end, a handling end disposed opposite to the insertion end, the handling end having an outer edge that comprises a convex region that extends an entire length of the outer edge of the handling end, wherein the insertion end is larger in size than the handling end, a first curved outer edge extending between the insertion end and the handling end, and a second curved outer edge extending between the insertion end and the handling end, wherein the second curved outer edge is disposed opposite to the first curved outer edge;

wherein the outer edge of the insertion end, the outer edge of the handling end, the first curved outer edge, and the second curved outer edge collectively form the entire circumference of the shield body;

wherein the first curved outer edge comprises a single concave region, and wherein the first curved outer edge is shaped to correspond to the contours of a floor of a patient's mouth along an anterior-posterior axis between inner surfaces of the patient's teeth and the patient's tongue;

wherein the second curved outer edge comprises a convex region extending an entire length of the second curved outer edge, and wherein the second curved outer edge is shaped to the contours of a roof of the patient's mouth along an anterior-posterior axis between inner surfaces of the patient's teeth and the patient's tongue;

wherein the shield body is configured and arranged such that when the insertion end is inserted into a first side of the patient's mouth, between inner surfaces of the patient's teeth and the patient's tongue, the first curved outer edge abuts the floor of the patient's mouth while the second curved outer edge simultaneously abuts the roof of the patient's mouth, and while at least a portion of the handling end extends outward from the mouth;

wherein the handling end is configured and arranged such that, when the insertion end is inserted into the first side of the patient's mouth, the portion of the handling end extending outward from the mouth is tuckable between outer surfaces of the patient's teeth and an inner surface of the patient's cheek on a second side of the patient's mouth, opposite to the first side of the patient's mouth, to isolate the patient's tongue and posterior pharynx from the first side of the patient's mouth:

wherein the oral shield comprises an anesthetic impregnated into the oral shield.

9. An oral shield for use in oral medical procedures, the oral shield comprising:

an absorbent, deformable shield body having a circumference, the shield body comprising an insertion end configured and arranged for insertion into a patient's mouth, the insertion end having an outer edge that comprises a convex region that extends an entire length of the outer edge of the insertion end, a handling end disposed opposite to the insertion end, the handling end having an outer edge that comprises a convex region that extends an entire length of the outer edge of the handling end, wherein the insertion end is larger in size than the handling end, a first curved outer edge extending between the insertion end and the handling end, and a second curved outer edge extending between the insertion end and the handling end, wherein the second curved outer edge is disposed opposite to the first curved outer edge;

wherein the outer edge of the insertion end, the outer edge of the handling end, the first curved outer edge, and the second curved outer edge collectively form the entire circumference of the shield body;

wherein the first curved outer edge comprises a single concave region, and wherein the first curved outer edge is shaped to correspond to the contours of a floor of a patient's mouth along an anterior-posterior axis between inner surfaces of the patient's teeth and the patient's tongue;

wherein the second curved outer edge comprises a convex region extending an entire length of the second curved outer edge, and wherein the second curved outer edge is shaped to the contours of a roof of the patient's mouth along an anterior-posterior axis between inner surfaces of the patient's teeth and the patient's tongue;

wherein the shield body is configured and arranged such that when the insertion end is inserted into a first side of the patient's mouth, between inner surfaces of the patient's teeth and the patient's tongue, the first curved outer edge abuts the floor of the patient's mouth while the second curved outer edge simultaneously abuts the roof of the patient's mouth, and while at least a portion of the handling end extends outward from the mouth;

wherein the handling end is configured and arranged such that, when the insertion end is inserted into the first side of the patient's mouth, the portion of the handling end extending outward from the mouth is tuckable between outer surfaces of the patient's teeth and an inner surface of the patient's cheek on a second side of the patient's mouth, opposite to the first side of the patient's mouth, to isolate the patient's tongue and posterior pharynx from the first side of the patient's mouth;

wherein the oral shield comprises an antibacterial agent impregnated into the oral shield.

\* \* \* \* \*